United States Patent [19]

Davis et al.

[11] Patent Number: 5,006,341
[45] Date of Patent: Apr. 9, 1991

[54] PROTECTION

[75] Inventors: Paul J. Davis, Bedfordshire; Simon C. Quarmby, Irchester, both of England; Albert W. Schoenmakers, Dendermonde, Belgium

[73] Assignee: Unilever Patent Holdings B.V., Rotterdam, Netherlands

[21] Appl. No.: 193,624

[22] Filed: May 13, 1988

[30] Foreign Application Priority Data

May 13, 1987 [GB] United Kingdom ............... 8711256

[51] Int. Cl.$^5$ ............................................. A23K 1/165
[52] U.S. Cl. ..................................... 424/442; 424/88; 424/93; 424/493
[58] Field of Search ............... 424/442, 88, 93, 493

[56] References Cited

U.S. PATENT DOCUMENTS

| 3,147,186 | 9/1964 | Edgar | 424/88 |
| 3,867,556 | 2/1975 | Darragh et al. | 424/493 |
| 4,343,826 | 8/1982 | McNaught | 426/601 |
| 4,544,548 | 10/1985 | Davis et al. | 424/93 |
| 4,639,372 | 1/1987 | Murray et al. | 424/88 |
| 4,724,145 | 2/1988 | Murray et al. | 424/88 |

Primary Examiner—Thurman K. Page
Assistant Examiner—P. L. Prater
Attorney, Agent, or Firm—Cushman, Darby & Cushman

[57] ABSTRACT

A composition useful in oral immunisation of animals such as poultry comprises dry free-flowing particles each consisting of a solid beadlet of lipid-continuous emulsion containing from about 25% to about 50% by weight water in a lipid, such as hardened palm kernel oil, having a slip point in the range 35° to 45° C., each beadlet having an average diameter of about 2 to 3 millimeters and containing at least 1 viable encysted protozoan, such as a sporulated oocyst of a species of coccidium infective to poultry, each beadlet having a protective coating of animal feed, cement and/or gypsum, the protective coating having an average thickness of about 0.2 to 2 mm.

19 Claims, 3 Drawing Sheets

PROTECTION

The present invention relates to the protection of sensitive material by entrapment within a relatively impervious coating.

The invention is particularly applicable to the protection of sensitive materials intended for oral administration to humans and animals, and especially to the protection of oral vaccine components such as live microorganisms. The invention will be described with particular reference to the protection of live encysted parasitic protozoa, such as coccidia oocysts, but from the following description the skilled reader will appreciate the utility of the invention in a wider context.

In the specification of U.S. Pat. No. 4544548 there is described a method for imparting immunity against coccidiosis in poultry by rearing the birds on a regular diet containing added viable sporulated coccidia oocysts at a level sufficient only to induce sub-clinical infection. An optional feature of the invention described in this U.S. patent is the encapsulation of the oocysts within an encapsulation material such as fat or wax, having a melting point in the range of about 30° to about 60° C. Such encapsulation can help to prevent dehydration of the oocysts, which are known to be sensitive to loss of moisture. The efficacy of a coccidiosis vaccine is dependent on the organisms still being viable when they are ingested by the bird.

The invention relates to ways in which the viability of oocysts incorporated in such a composition can be further enhanced.

The invention provides a composition comprising solid particles of a lipid-continuous emulsion of at least 1% by weight of water in lipid having a melting point in the range 30° to 55° C., the composition containing per article an average of at least 1 live encysted parasitic protozoan.

The invention also provides a process for the preparation of an orally administrable composition, comprising encysted parasitic protozoa entrapped within a coating of lipid, which process comprises the steps of
(a) preparing a dispersion of the encysted parasitic protozoa in a lipid-continuous emulsion, the lipid having a melting point in the range 30° to 55° C. and the emulsion being in the liquid state and at a temperature not exceeding 60° C.; and
(b) causing the emulsion to set by cooling.

Figure 1:
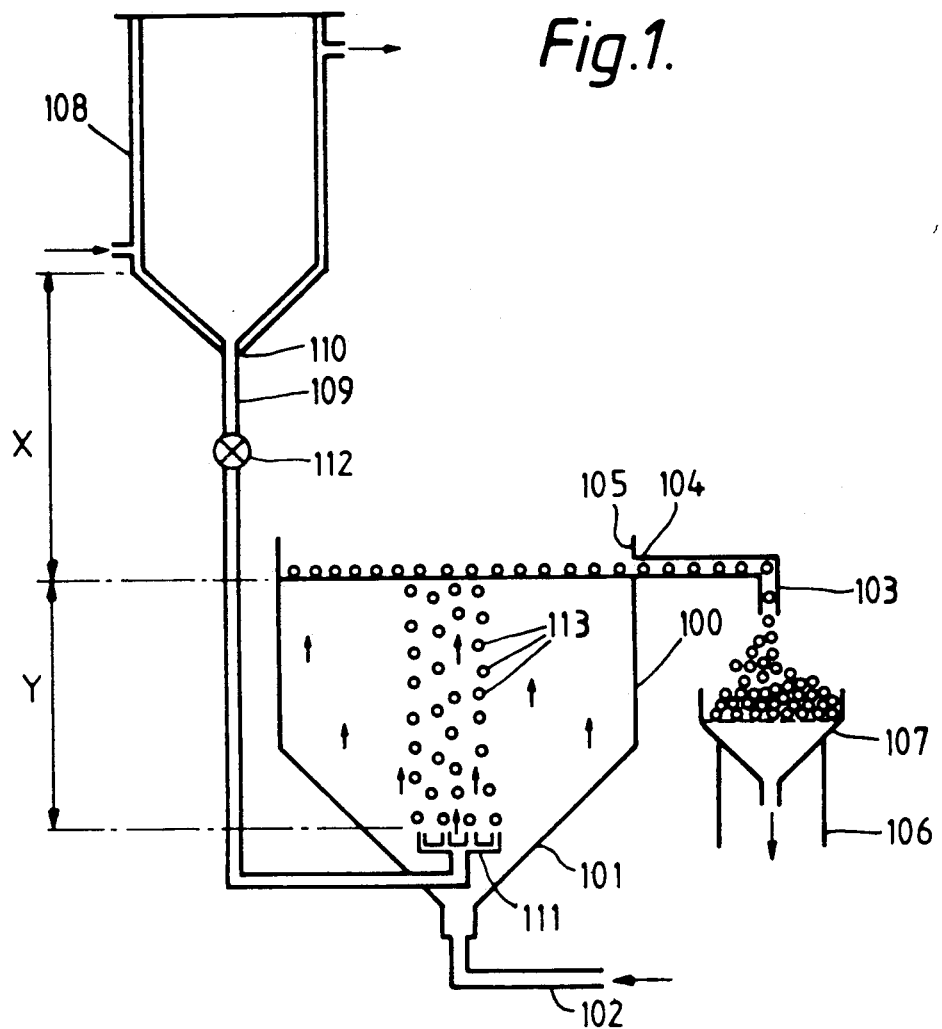
FIGS. 1-6 depict various types of equipment which may be used in the encapsulation of the oocysts.

Generally the lipid will be a fat or wax. Blends of fats and/or waxes can be used if desired. The proportion of water in the emulsion should not be so great that the lipid-continuous property is not retained when the emulsion is set, otherwise the protective effect of the fat or wax will be lost. Preferably the water content of the emulsion will not exceed about 70% by weight, and more preferably will not exceed about 50% by weight. A moisture content of from about 1 upwards can be used, and a moisture content in the range of about 25% to about 50% by weight of the emulsion is ideal. The use of such an emulsion provides the protective properties of the fat or wax together with an abundant supply of moisture in which the oocysts can survive for a prolonged period.

Preferably the fat or wax has a melting point not exceeding 50° C.

In order to facilitate processing of the emulsion, it should be stable in liquid form. Preferably this stability should be for at least five minutes, and ideally for at least 30 minutes. In view of this requirement, the dispersion of the oocysts in the emulsion should be achieved using high speed mixing equipment. The types of equipment used in processing many conventional water in oil emulsions, such as the votators used in the margarine industry, are unsuitable because they are primarily designed for handling solid emulsions.

The desired emulsion can be prepared by blending a suitably dilute aqueous suspension of oocysts with the molten fat or wax, or by combining a relatively more concentrated oocysts suspension with the molten fat or wax, together with sufficient additional moisture to achieve the final desired composition. Preferably, in order to avoid exposing the oocysts to prolonged mixing which might result in heat damage to the sensitive organisms, it is preferable that an initial aqueous emulsion is prepared, and the oocysts added to this in a second mixing stage.

Following the preparation of the oocyst-containing liquid emulsion, the emulsion can be set to provide a solid composition. This can be achieved by allowing the emulsion to set in bulk, and the resulting solid mass can be subdivided, e.g. by low pressure extrusion, to provide a composition in particulate form.

Preferably however, a particulate composition is prepared from the liquid emulsion by subdividing the emulsion into small portions before it is set. This considerably facilitates the manufacture of a composition in which the particles are of uniform and attractive appearance.

In one embodiment of the invention, the molten emulsion is spray-cooled ("spray-dried"). This tends to produce very small particles which may be suitable for blending with other feed ingredients and processing further to provide a composite feed formulation.

If it is desired to produce a particulate composition of the invention which can be added to a granular feed composition, e.g. a poultry feed, it is preferable that somewhat larger particles are produced.

The invention provides as a preferred embodiment, a process which includes the step of exposing the molten emulsion to a comparatively cold environment to provide solid particles or "noodles" of the set wax or fat, having a minimum dimension of least 2 mm.

Preferably the resulting solid composition is in the form of granules which may, if desired, be of more or less spherical shape. Preferably the maximum dimension of such granules does not exceed 10 mm, and ideally is in the range of 2 to 5 mm. When such granules are incorporated in a particulate feedstuff for poultry, spherical granules having a diameter of 2 to 5 mm, e.g. about 3 mm, are ideal because they are less prone to separate from the bulk feedstuff during handling and storage. In this context particles having maximum dimension of substantially less than 2 mm should be avoided because they will readily separate from conventional granular feedstuffs.

Preferably the setting of the molten emulsion is achieved by contact with chilled water. This can be achieved by releasing a stream of the molten emulsion into a volume of cold water, or by allowing the molten emulsion to fall as droplets of appropriate size into a volume of cold water.

If desired, the cold water can incorporate a surface active agent, such as a nonionic surfactant, to lower the surface tension and to encourage the molten emulsion to resolve itself into droplets of uniform size and shape which when set will comprise a more uniform and attractive product.

The fat or wax is preferably fully molten below 50° C., so that the encysted parasitic protozoa are not damaged. The fat or wax should be solid at the ambient temperatures at which the product will be stored and used, e.g. in the range 20° to 30° C. Fats and waxes having a slip point in the range 35° to 45° C. are ideal. Preferably the slip point should be as sharp as possible. Hardened palm kernel oil is a very suitable material, and is available commercially with a range of slip points, e.g. about 39° C. and about 42° C.

When the invention is applied in the preparation of an oral composition for poultry containing coccidia oocysts, either mixed with feed or as a separate composition, it is important that the number of viable oocysts administered should be at a level that will induce effective immunity. Preferably the composition should be formulated such that all birds consuming it will ingest oocysts from the first day. Preferably each particle of the composition should contain, on average, at least one viable oocyst. However, much higher levels can be incorporated per particle, depending on many factors such as the intended mode of administration, and the virulence of the oocysts used. It is therefore impossible to specify an absolute upper limit. Purely as a guide, however, we can say that when used as an oral vaccine each particle should contain, on average, from 1 to about 10,000 viable oocysts at the time of administration. Generally, the inclusion level, for use as an oral vaccine, should be an average of from 1 to about 2,000 oocysts per particle. These figures are per species of coccidia present in the composition, and it will be appreciated that compositions containing multiple species can be used to confer broader immunity.

If the invention is used as a means for storing and handling oocysts conveniently, even larger numbers of oocysts can be incorporated if desired. In this form the composition may not be suitable for immunizing, although it could be used to administer oocysts in a challenge to test immunity, or to administer a large dose of oocysts as part of a passaging routine.

It is normal practice for oocysts to be stored as an aqueous suspension, and this can be used in the preparation of the emulsion. Provided that high speed mixing is not conducted for a prolonged period, we have found that the oocysts are not apparently damaged thereby, and hence no significant loss of viability is attributable to such treatment.

If desired, the flow properties of the fat or wax particles can be enhanced by coating them with a dry powder. Examples of suitable materials are powdered animal feeds, flour, and powdered edible inorganic materials. Inorganic powders which can form a hard composition when moistened and dried are especially suitable. Cement provides an excellent coating. Gypsum (calcium sulphate) is also very suitable. Mixtures of coating materials can be used. Inorganic coating materials are preferred, as there is less risk of spoilage during storage. Inorganic powders such as cement and gypsum form a hard protective layer on the outside of the emulsion particle, so providing a very robust, free-flowing product. Despite the hardness of such a coating, we have found that the oocysts are easily released from the composition by the normal digestive processes in poultry. Such materials are usually white, but a colouring agent such as an edible dye or pigment, or a naturally coloured feed component such as molasses, can be added if desired. The coating should be applied in sufficient quantity to provide a protective layer of at least about 0.1 mm thickness on the individual fat emulsion particle. Preferably the coating has a thickness in the range of about 0.2 mm to about 2 mm. When the coating material is cement or gypsum, the thickness of the coating is preferably in the range of about 0.2 mm to about 0.5 mm. An optimum composition according to the invention will comprise solid fat emulsion particles having an average diameter of about 2–3 mm, protected by a coating of average thickness about 0.5 mm. In order to provide a coating that adheres firmly to the particles, a binder such as malto-dextrin or molasses can be used, but in many instances water alone is effective.

The coating may be applied by tumbling the fat particles in an open vessel, spraying water or binder solution onto the tumbling particles while simultaneously adding the powdered material, and continuing this procedure until a sufficiently thick coat of the powdered material has formed. Drying may be needed in order to harden the coating. A spheroniser is a particularly suitable device in which the coating can be applied. This comprises a disc which can be rotated about a substantially horizontal axis at high speed, and surrounded by a stationary cylinder. Particles placed inside the spheroniser are thrown against the stationary wall by the high rotational speed of the disc. When water or binder solution is sprayed onto the particles and dry coating powder is applied, the high shear force is generated inside the apparatus prevent the particles agglomerating.

An important preferred embodiment of the invention is a composition comprising dry free-flowing particles each consisting of a solid beadlet of lipid-continuous emulsion containing from about 25% to about 50% by weight water in a lipid having a slip point in the range 35° to 45° C., each beadlet having an average diameter of about 2 to 3 millimeters and containing at least 1 viable sporulated oocyst of a species of coccidium infective to poultry, each beadlet having a protective coating of cement and/or gypsum, the protective coating having an average thickness of about 0.2 to about 0.5 mm.

In one embodiment of the invention, the composition contains live encysted parasitic protozoa and a chemotherapeutic agent effective against the protozoa at an intermediate stage in their life cycle, in an amount sufficient to prevent full development of the protozoa in a host following ingestion. The parasitic protozoa are therefore able to establish themselves briefly in the host following ingestion, so leading to an immune response in the host, but the protozoa are prevented by the chemotherapeutic agent from achieving a full life cycle leading to the release of infective protozoa into the environment. For example, if the protozoa are coccidia, this embodiment will ideally utilize an anticoccidial drug believed to have its peak effect at a late stage in the life cycle of the coccidia, preferably during late schizogony. Examples of appropriate anti-coccidial drugs are nicarbazin, furazolidone, nitrofurazone, nihydrazone, sulphaquinoxalene, sulpanitran, dinsed, ormetroprim, sulphadimethoxine and ethopabate. The administration of a vaccine containing a chemotherapeutic agent prevents transmission of the parasite to other hosts, without allowing drug resistant strains to develop. The presence of the chemotherapeutic agent provides a further safeguard against any possibility that the administration of the infective protozoa might lead to a clinical infection in the host under unusual circumstances. Fully virulent protozoa and/or attenuated protozoa can be used in combination with chemotherapeutic agents, if desired.

Administration of the vaccine of the invention can be achieved in a number of ways, such as:

(a) Incorporate in a feedstuff for the host, by blending with nutrient materials during feed manufacture. If desired, a pre-mix containing the composition of the invention, in particulate form, can be used to facilitate distribution of the protozoa-containing particles throughout the bulk of the feedstuff.

(b) Simple addition to feed at the same time as the feed is presented to the host, e.g. by sprinking particles onto poultry feed.

(c) Individual administration to host animals, such as newly-hatched poultry chicks.

The vaccine of the invention can be based on a single strain or species of protozoa, but more preferably broad host-specific immunity should be aimed for by including a selection of common strains or species of protozoa in a single vaccine formulation. The protozoa used can be fully virulent "wild" strains, attenuated strains (e.g. embryo-adapted strains or precocious strains), interbred strains (currently available for certain coccidia, such as *Eimeria maxima*), or strains that have been modified by genetic manipulation, for example. A single vaccine formulation can include a combination of these different strain types, if desired.

The invention will be described particularly in relation to the control of coccidiosis, but it will be readily apparent to the skilled reader that compositions imparting immunity against other cyst-forming parasitic protozoa can be produced by means of the invention.

The invention can be applied to the control of coccidiosis in any host species that is prone to suffer from the disease. Although long associated with avian species, especially poultry, coccidiosis is now being recognized as important in a much wider range of species. Intensive farming methods have tended to magnify the incidence and seriousness of its outbreaks. Examples of non-avian host animals in which coccidiosis is now recognized as being a problem are pigs, ruminants (especially cattle, sheep and goats) and rabbits. The disease is not usually a serious factor in the health of the adult animal, but can be very damaging to the neonate born into an environment heavily contaminated by the mother.

Coccidiosis has been studied extensively in poultry, but has so far received relatively little attention in other species. Accordingly, comprehensive details of the coccidia that infect pigs, for example, are not available although several coccidia have been identified in the literature. For instance, the following coccidia have been observed in pigs: *Eimeria debliecki, E.scabra, E.- suis, E.spinosa, E.perminuta, E.neodebliecki, E.porci, E.cerdonis, E.polita* and *Isospora suis*. Specific bovine coccidia that have been identified are: *Eimeria bovis, E.zuernii, E.ellipsoidalis, E.auburnersis, E.cylindrica, E.alabamensis* and *E.bukidnonensis*. Sheep are infected by: *Eimeria minakohlyakimovae, E.ovina, E.intricate* and *E.ahsate*. Goats are infected by *E.arloingi*. Coccidia that have been recorded in rabbits are: *Eimeria intestinalis, E.flavesens, E.magna, E.irresidua, E.periformis, E.stiedai, E.perforans, E.neoleporis* and *E.media*.

The invention will, however, be more particularly described in relation to poultry. In this specification, the term "poultry" is used to denote birds of the order Galliformes such as the ordinary domestic fowl or chicken (*Gallus domesticus*), turkeys (Meleagris), pheasants (Phasianus), partridges (perdix), grouse (Lagopus), guinea fowl (Numida) and peacocks (Pavo), and also birds of the order Anseriformes such as ducks (Anas) and geese (Anser).

The domestic fowl (*Gallus domesticus*) can be infected by any of the coccidia *Eimeria tenella, E.necatrix, E.brunetti, E.maxima, E.Acervulina* and *E.praecox*. The following coccidia are implicated in infections of turkeys (Meleagris): *Eimeria melagrimitis, E.dispersa, E.- meleagridis, E.gallopavonis, E.adenoides, E.innocua* and *E.subrotunda*. Domestic ducks (Anas) suffer from infection caused by *Tyzzeria perniciosa* and also, it is believed by *Eimeria anatis* which they can acquire from wild ducks (*Anas platyrhyncos*). Geese (Anser) can suffer from infections caused by *Eimeria anseris, E.nocens* and *E.parvula*, and in addition it is believed that domestic geese can pick up infections from Canada geese caused by *Eimeria hermani, E.striata* and *E.fulva*. The other poultry species referred to earlier each suffer from infections caused by characteristic coccidia, and the invention is equally appropriate and effective in the control of infections caused by the characteristic coccidia in such other poultry species. All oocyst levels mentioned in this specification should be construed as being per coccidia species present.

Coccidial infections are encountered in all poultry species that are reared by man. Such infections are particularly troublesome when they occur in flocks of birds reared under modern intensive husbandry conditions. Infection can spread rapidly throughout the flock, and at the very least can cause poor growth. Severe infection can lead to death of the birds. Thus for many years considerable effort has been expended in attempts to find reliable prophylactic measures against such infections, and in particular to find ways in which birds can be immunized effectively against the incidence of such infections. The practical benefit of any effective immunizing technique will be to promote the growth of poultry to which immunity is imparted, at least in the sense that the negative effects on growth caused by coccidial infections will be counteracted thereby.

By providing poultry with oocysts in their regular feedstuff, the poultry are able in effect to conduct a controlled progressive self-inoculation. Daily intake of oocysts is dictated by the quantity of feedstuff eaten by each bird, and the level of oocysts in the feedstuff can be regulated by the feedstuff manufacturer whose sophisticated quality control facilities can readily ensure that no risks of overdose can possibly arise. Moreover, by having the oocysts in their normal diet, it is possible to ensure that the chicks are consuming appropriate levels of oocysts as soon as they begin to ingest solid food, and thus the immunizing process can begin at a very early moment in their post-hatching life.

The viable sporulated oocysts can be obtained by deliberately infecting host animals such as a donor flock of birds, and collecting the oocysts from their droppings. Techniques for obtaining viable sporulated coccidia oocysts per se are well known in the art, and form no part of the present invention. One suitable procedure is described at length in U.S. Pat. specification No. 3 147 186.

With regard to the level of oocysts to be administered, e.g. via the feedstuff, preferably the feedstuff will contain not more than about 2,500 viable sporulated oocysts per kg. Although positive benefits will be obtained by the introduction of the sporulated oocysts into the feedstuff given to an individual bid at any stage of its life, it is preferable that the bird is provided with a feedstuff containing the low levels of sporulated oocysts as soon as it has been hatched and commences feeding. As the bird grows, its daily food requirement increases dramatically. Taking the domestic fowl (*Gallus domesticus*) as an example, at the "first feeding" stage the chick will consume at least about 2 g of feedstuff per day. After 10 days this will have risen to at least about 10 g per day, and after 30 days the bird will be consuming perhaps 80 g or more per day. The nutritional requirements of the bird change as it develops, and commercially-available poultry feedstuffs are sold with a range of formulations intended for the different stages of the bird's development. Typically such a range will include feedstuffs specifically formulated for "Starters", "Growers" and "Breeders/layers". In order to ensure that at each stage of its development the bird is consuming an appropriate number of sporulated coccidia oocysts per day, it may be appropriate for the different feedstuffs to contain different numbers of oocysts per kg.

For optimum immunization, we believe that a newly-hatched chick should consume about 1 to 20 viable sporulated oocysts per day. During the first 10 days of growth, this level should rise to about 2 to 50 oocysts per day. By day 30, the level of oocysts consumed per day should be of the order of about 5 to 200.

Preferably a "starter" feedstuff will contain at least about 50 viable sporulated oocysts per kg. Preferably the maximum level of oocysts will be about 5,000 per kg, and ideally not more than about 2,000 per kg. In a "grower" feedstuff the minimum level of viable sporulated oocysts is preferably about 50 per kg. The upper level of oocysts is preferably about 2,000 per kg, and ideally not more than about 500 per kg. In a "breeder/layer" feedstuff an appropriate minimum level of viable sporulated oocysts is about 10 per kg. Preferably the upper level of oocysts does not exceed about 1,000 per kg, and ideally is not greater than about 100 per kg.

For host species other than poultry, the daily intake of coccidia oocysts may need to be different depending on factors such as the relative virulence of the organism and the size and susceptibility of the animal involved. In the weaned calf, for example, a daily intake of 1-100 viable sporulated oocysts is probably sufficient.

Certain parasitic protozoa have as their transmission stage "cysts within cysts". Coccidia, for example, exist as sporocysts within an outer cyst (the oocyst). Although for practical purposes it is more convenient to use the whole oocyst as the vaccine ingredient, it will be possible to incorporate released sporocysts in a fat emulsion. We therefore contemplate the use of sporocysts in a vaccine in accordance with the invention, although normally oocysts will be preferred.

It will be appreciated that compositions according to the invention can be used also to aid the incorporation of other essential trace ingredients in a feedstuff, for example, mineral additives which are important especially in promoting egg-shell formation in laying birds, growth promotors, vitamins and amino acids such as lysine, and carotenoid pigments commonly used to influence the colour of egg yolks. If desired, one or more of these minor ingredients can be included with the oocysts together in one composite composition.

A composition of the invention can be incorporated in a feedstuff by simple admixture, the proportion of composition per unit weight of the feedstuff being chosen with regard to the concentration of the oocysts present in the composition and the concentration of the oocysts desired in the feedstuff. Apart from the inclusion therein of the composition containing the viable sporulated oocysts, it is not essential for the composition or physical form of a feedstuff to be altered in putting the invention into effect. Any of the currently standard "complete" or nutritionally balanced commercial feedstuff formulations can be used, and the nutrient material in the feedstuff can thus comprise any of the protein, carbohydrate and fat ingredients normally found in such feedstuffs. The nature of such standard ingredients, such as the various fish meals, milled grain and other plant material, and mineral additives, and the nutritional requirements such as minimum levels of vitamins, amino acids and trace elements, are well known in the art and documented in the technical literature, and such details forms no part of the present invention.

The following techniques, which are given by way of example only, illustrate ways in which compositions according to the invention can be prepared.

EXAMPLE 1

Figure 2:
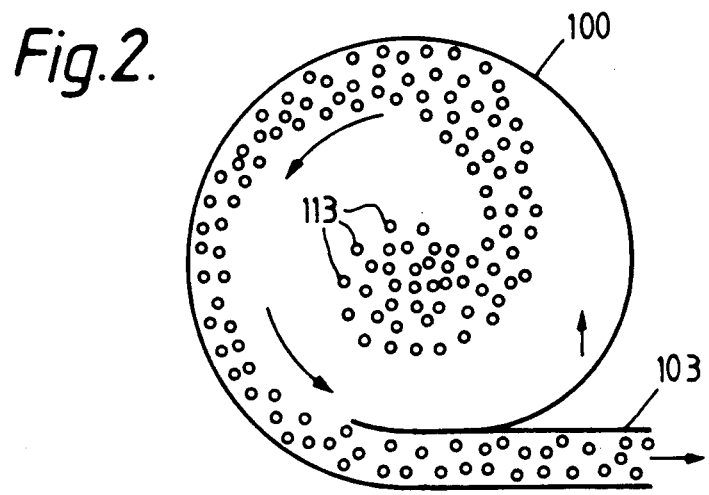

FIGS. 1 and 2 of the accompanying drawings illustrate an apparatus in which a product according to the invention can be prepared.

Referring to FIG. 1, the apparatus comprises an upright open-topped cylindrical container 100 for water, having a downwardly projecting conical base 101 into the center of which a cold water inlet 102 runs. An overflow channel 103 extends from a point 104 at the periphery of the top 105 of the container, and leads over a drain 106 on which is mounted a sieve 107 to catch any particulate matter carried with water overflowing from the container 100. A water-jacketed storage container 108 for molten fat emulsion is situated above the level of the top of the water container, and a supply pipe 109 leads from the base 110 of the storage container 108 into the lower regions of the conical base 101 of the water container 100 and terminates in a plurality of upwardly pointing nozzles 111. The flow of molten emulsion from the storage container 108 to the nozzles 111 can be controlled by means of a valve 112 in the supply pipe 109.

FIG. 2 represents a downward view of the top of the water container 100, and shows the overflow system 103 leaving tangentially from the side of the container.

In operation, a continuous stream of cold water is admitted to the bottom of the water container 100, such that a steady gentle flow of water passes through the outflow 103 and falls into the drain 106 via the sieve 107. A molten fat emulsion, containing dispersed encysted parasitic protozoa, is place in the storage container 108. Heights X and Y are adjusted such that when the control valve 112 is opened and the liquid emulsion can flow down towards the nozzles 111. The streams of liquid emulsion emerging from the nozzles 111 are just sufficient to provide a steady production of small fat droplets 113 forming at the nozzles 111 and rising through the water to the top of the water container 100. While ascending through the chilled water, the fat droplets 113 will solidify and provide the encapsulated product of the invention. On arrival at the water surface, the solidified droplets will be carried via the overflow system and will collect in the sieve. The application of an airstream to the water surface, as shown in FIG. 2, will cause the droplets, which arrive at the water surface near the vertical axis of the container, to circulate around the periphery of the container until they enter the overflow system.

Optional modifications, which may be used in combination if desired, to this procedure are:
(a) The use of a pumped emulsion delivery system, rather than simple gravity feed.
(b) The use of heated nozzles, which may assist discrete fat emulsion droplet formation.
(c) The application of a pulse, e.g. by means of a vibrator, to the fat emulsion delivery pipe 109, which may also assist discrete droplet formation.
(d) Having the water in vessel 101 essentially static, but adding water at the top of the vessel to provide an overflow current to carry the fat particles into the overflow system.

EXAMPLE 2

Figure 3:
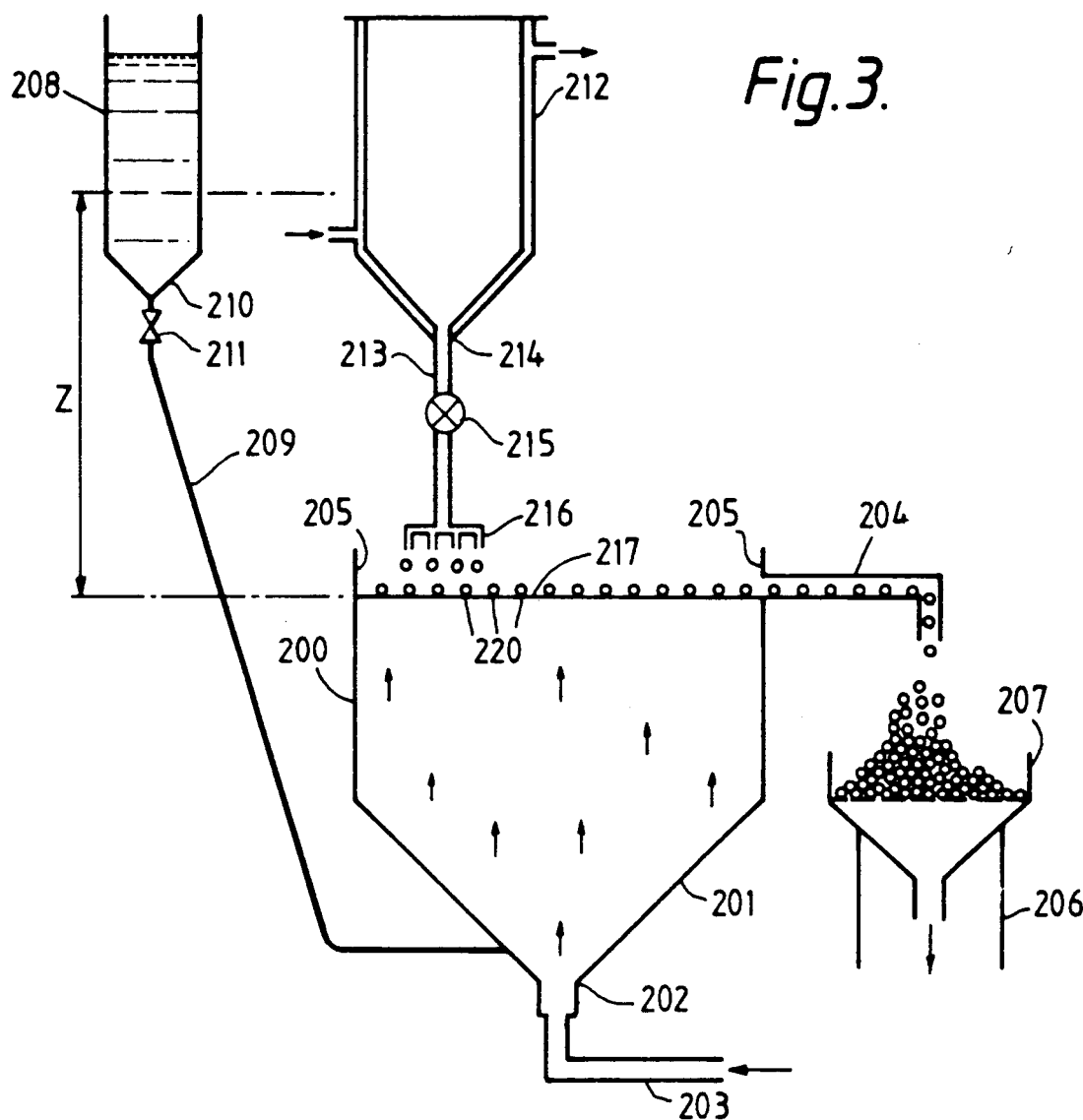
Figure 4:
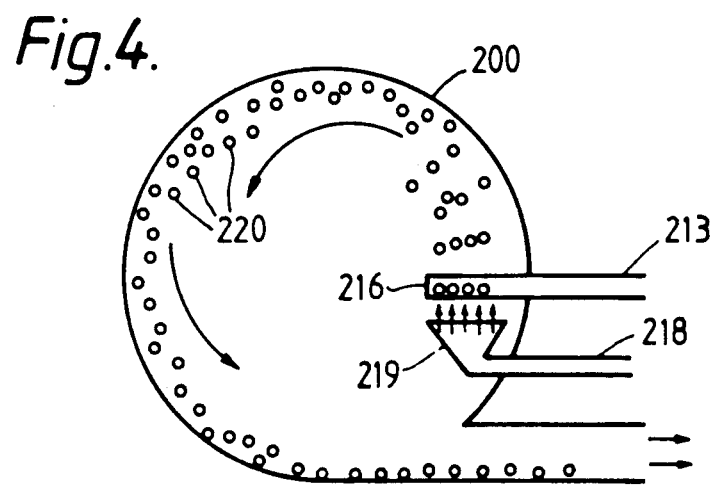

FIG. 3 and 4 of the accompanying drawings illustrate an alternative apparatus which can be used in accordance with the invention.

The apparatus shown in FIG. 3 comprises an upright open-topped cylindrical water container 200 having a downwardly pointing conical base 201 into the center 202 of which runs a cold water inlet 203. An overflow system 204 leads from the periphery of the top 205 of the water container 200, and flows into a drain 206 via a sieve 207. A storage container 208 for surfactant solution is located above the level of the top of the container 200 and a feed pipe 209 leads from the base 210 of the storage container, via a control valve 211, into the lower regions of the water container 200 adjacent the water inlet 203.

A water-jacketed storage tank 212 for molten fat emulsion is provided above the level of the top of the water container 200. An outlet pipe 213 leads from the base 214 of the emulsion storage container 212, downwardly via control valve 215 to a plurality of nozzles 216 located a short distance above the water surface 217 in the water container 200 and adjacent the periphery 205 of the container 200.

FIG. 4 represents a downward view of the top of the water container 200 and shows the overflow 204 extending tangentially from a point on the periphery 205 of the container. In FIG. 4, the feedpipe 213 from the liquid emulsion storage tank 212 is shown diagrammatically, as also is a pressurized air line 218 terminating in a series of horizontal jets 219 from which an airstream can be directed onto the surface 217 of the water in the water container 200. This airstream blows past the fat emulsion nozzles 216 and will cause a current of water to circulate at the top of the water container away from the nozzles and around the periphery of the container towards the overflow system 204.

In operation, a stream of cold water is admitted to the base of the water container 200, such that a gentle flow of water will be carried through the overflow system 204 and down into the drain 206 via the sieve 207. A slow bleed of surfactant solution will be admitted to the lower regions of the water container 200 and will mix with the inflowing cold water. A molten fat emulsion, containing dispersed encysted parasitic protozoa, will be place in the storage tank 212. By appropriate adjustment of height Z, this emulsion can flow via the control valve 215 to the nozzles 216 and emerge as droplets 220 which fall onto the surface of the water. The presence of the surfactant in the water will ensure that these droplets remain coherent and will not disperse to form a continuous layer or film on the water surface. After falling onto the water surface, the droplets will be carried away from the nozzles by the circulating current generated by the applied airstream. During their journey from the nozzles to the overflow system, the molten emulsion droplets will solidify in the chilled water and will collect in the sieve after leaving the overflow.

EXAMPLE 3

Figure 5:
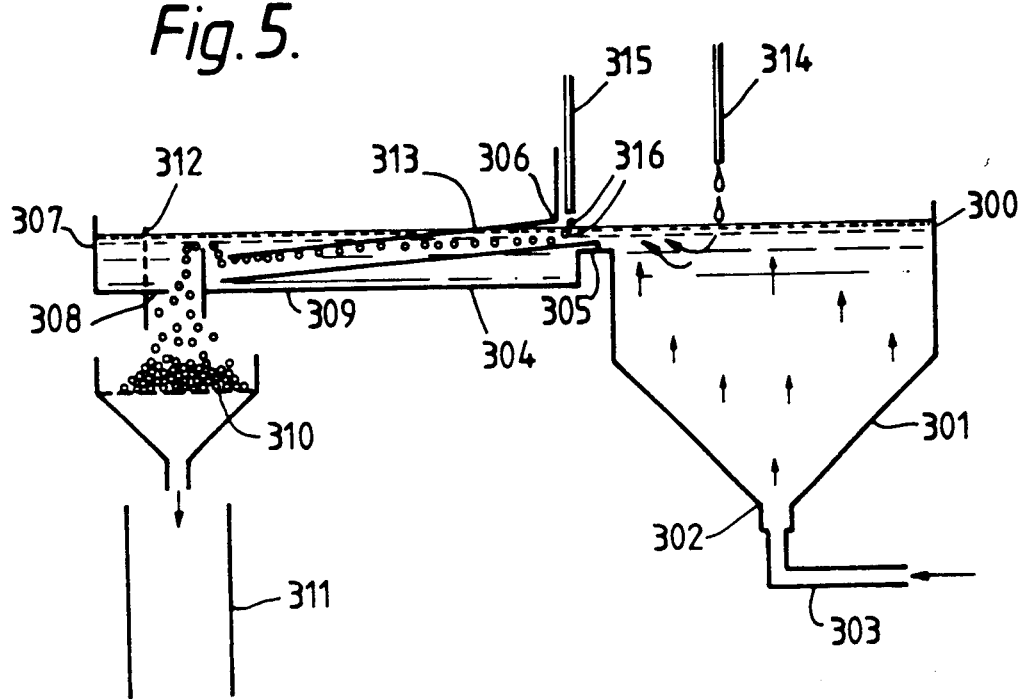

FIG. 5 of the accompanying drawings illustrates a further apparatus in which a product in accordance with the invention can be made.

The apparatus comprises an upright open-topped cylindrical water container 300 having a downwardly projecting conical base 301, into the center 302 of which runs a cold water inlet 303. A horizontal trough 304 extends laterally from a lip 305 in the top 306 of the water container 300. The lip 305 is lower than the remainder of the 306 top of the water container 300, and accordingly any overflow of water from the water container must pass over the lip and into the trough. Adjacent the end 307 of the trough remote from the container 300 is an aperture 308 in the trough floor 309 through which water can escape via a sieve 310 and into a drain 311. The outlet is surrounded by a perforated baffle 312 extending upwardly towards, but not as far as, the top of the trough. Any particulate matter in the water in the trough must ride over this baffle before escaping with the water through the outlet.

A pipe 313 extends at a slight downward angle from the lip 305 into the trough 304, and terminates near the baffle 312 surrounding the water outlet 308. The pipe 313 is arranged such that at the lip end it is partly above and partly below the water level in the container and trough, whereas adjacent the baffle 312, the other end of the pipe is totally submerged in the water. Water flowing over the lip from the water-container is thus constrained to flow down through the pipe before emerging adjacent the baffle.

The apparatus also comprises a pipe 314 located above the water-container, from which surfactant solution can be added to water in the container 300.

Finally, a pipe 315 for molten fat emulsion is located above the end of the trough 304 immediately adjacent the lip 305 such that droplets of fat emulsion emerging from the pipe 315 are immediately carried by water overflowing from the water-container 300 into the guide pipe 313 and hence down towards the baffle 312 in the trough.

In operation, a steady flow of cold water is admitted to the base of the water container 300, such that a gentle stream of water overflows into the trough 304 via the guide pipe 313. Droplets of surfactant solution are applied to the top of the water-container, where they blend with the water to provide a dilute surfactant solution flowing over the lip 305 into the trough. Molten fat emulsion droplets 316, containing dispersed encysted parasitic protozoa, are applied to the water in the immediate vicinity of the guide pipe 313 through which they will be carried by the water flow. These droplets will solidify in the cold water during their passage through the guide pipe. On emerging from the end of the guide pipe, the solidified droplets will be carried over the baffle 312 and fall to be collected on the sieve 310.

EXAMPLE 4

Figure 6:
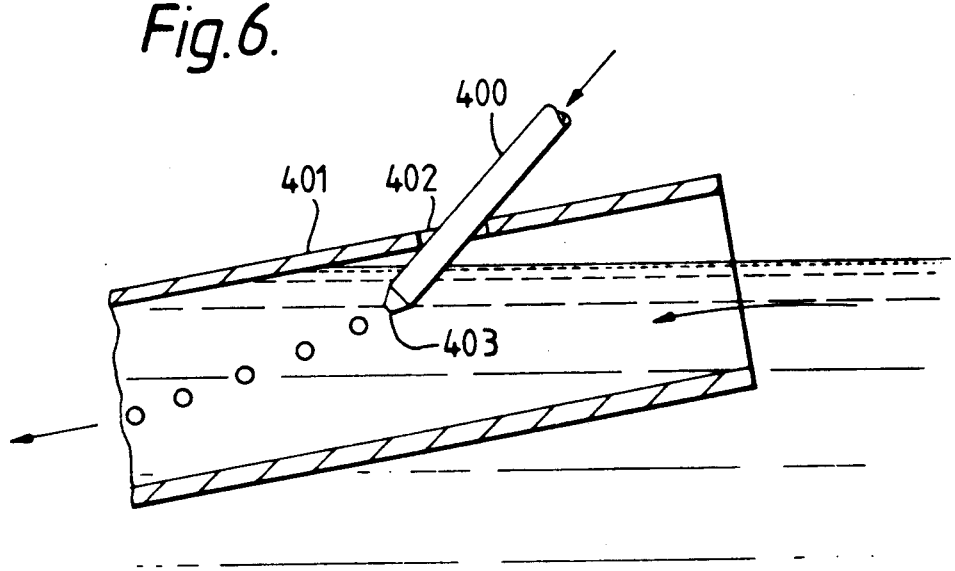

FIG. 6 of the accompanying drawings illustrates a modification of the apparatus shown in FIG. 5.

In this variation the apparatus operates in exactly the same manner as that depicted in FIG. 5, except that the molten emulsion is injected below the water level through a pipe or needle 400 which penetrates the guide pipe 401 through an orifice 402. Nozel 403 at the bottom end of pipe 400 is below the level of water flowing from the water vessel (not shown) into the guide pipe 401.

Uniform solidified spherical particles of the emulsion can be formed easily using this modification, and the size of these particles can readily be adjusted by altering the flow rate of the water and of the liquid emulsion.

EXAMPLE 5

A composition according to the invention, in the form of solid beadlets of water in oil emulsion containing viable sporulated oocysts of the coccidium *Eimeria tenella*, were prepared using the technique described above under Example 2.

The fat used was a commercially available hardened palm kernel oil having a slip point of 39° C. This was emulsified with water to provide two emulsions (compositions A and B) containing 8% and 16% by weight water respectively. To each emulsion was added 0.6% by weight of an aqueous oocyst suspension containing about 26,000 oocysts per ml. The final composition of each emulsion therefore contained about 8.5% and 16.5% by weight water respectively, and each emulsion contained about 15,600 oocysts per 100 ml. As a control composition, 0.6% of the same aqueous oocyst suspension was added to the palm kernel oil as commercially obtained, hence giving an emulsion containing about 0.5% water and about 15,600 oocysts per 100 ml. In the table below this control composition is identified as composition C.

The initial emulsification was performed in a conventional emulsion mixer (Turox). The emulsions were stabilized using 0.5% Admul WOL stabilizer. The oocyst-containing aqueous suspension was blended with the resulting emulsion, at about 45°-50° C., using the same equipment for about 20 seconds.

The oocyst-containing beadlets were formed by dropping the molten emulsion from 0.8 mm internal diameter needles through a distance of 1 cm onto cold water (15° C.) containing 300 ppm of nonionic surfactant (Synperonic 7EO). A flow rate of 7.2 liters/minute of water was maintained. After recovery from the water, the beadlets were dried overnight at room temperature. Beadlets of approximately 4 mm diameter were obtained and these contained on average about 5 oocysts each.

The beadlets were stored for two weeks at 4° C. and thereafter mixed with a commercially available poultry feed and stored for a further four weeks at ambient temperature. The viability of the oocysts was tested at the end of the 4° C. storage period, and also after two weeks and four weeks in-feed. The viability was assessed by administering the composition to poultry (beadlets or feed containing the beadlets) under challenge conditions and monitoring the oocyst output over the subsequent 10 days.

The results, expressed in terms of the total oocyst output per bird, are given in Table 1 below. The reproductive index (RI) is also given, i.e. the number of oocysts produced per oocyst administered. These results show that although viability was declining, significant viability remained even after four weeks in-feed at ambient temperatures in the beadlets that had been prepared from the 8% and 16% water emulsions. In contrast, although the viability of the oocysts in the control composition prepared from straight fat showed good viability after two weeks in-feed at ambient temperatures, following a further two weeks storage the viability had declined seriously.

EXAMPLE 6

Further compositions according to the invention, in the form of solid beadlets of water-in-oil emulsion containing viable sporulated oocysts of *Eimeria tenella*, were prepared using the technique described above under Example 4.

Emulsions were prepared from commercially available hardened palm kernel oil (PK 39) molten at 60° C., with distilled water and 1% Admul WOL emulsifier. After the emulsion had been allowed to cool to a temperature below 50° C., aqueous oocyst suspension was added. The entire operation was conducted in a standard laboratory high speed mixer. In practice, the nature of the mixing equipment is not critical. The quantities of water and aqueous oocyst suspension added to the mixture were calculated to provide two final compositions containing 8% and 25% water respectfully (compositions D and E).

Oocyst-containing beadlets were prepared from these compositions by injecting the emulsion at 45°-50° C. at 800 g per hour through a 1 mm internal diameter needle into water at 19° C. flowing at approximately 10 cm per second. Under these conditions beadlets of approximately 4 mm diameter were produced. The beadlets of composition D contained on average 214 oocysts each and those of composition A contained on average 183 oocysts.

The oocyst-containing beadlets were stored in dessicators over water (100% RH) at ambient temperature for several weeks, and also over poultry feed (about 65% RH) under the same circumstances. During this period the viability of the oocysts was determined at weekly intervals by administering beadlets to poultry. In each instance, ten beadlets were given to each of a group of five 2-week old birds. In terms of the oocyst dose, this represented a serious challenge and the oocyst output from the resulting infection was monitored. The results, expressed as the total oocyst output ($\times 10^6$) per bird over 5 days, are given in Table 2 below. These show that the oocyst viability remained at a high level for at least three weeks, and that significant numbers of the oocysts were still viable after 5 weeks.

EXAMPLE 7

Further compositions according to the invention, in the form of solid beadlets of water-in-oil emulsion containing viable sporulated oocysts of *Eimeria tenella*, were prepared using the technique described above under Example 1.

Emulsions were prepared from commercially available hardened palm kernel oil (PK 39) molten at 60° C., with distilled water and 1% Admul WOL emulsifier. After the emulsion had been allowed to cool to a temperature below 50° C., aqueous oocyst suspension was added. The entire operation was conducted in a standard laboratory high speed mixer. In practice, the nature of the mixing equipment is not critical. The quantities of water and aqueous oocyst suspension added to the mixture were calculated to provide two final compositions each containing 25% water, but containing different levels of oocysts such that approximately 100 oocysts would be contained in a 2 mm diameter bead (Composition F) and a 4 mm diameter bead (Composition G).

Oocyst-containing beadlets were prepared from these compositions by pumping the emulsion at 45°-50° C. through a 0.5 mm internal diameter nozzle into water at 4° C.

For Composition F, the emulsion was pumped to the nozzle at a flow rate of 0.5 kg/hour. This resulted in the emulsion emerging from the nozzle under jetting flow conditions, and the natural vibration induced by the pump caused beadlets of about 2 mm diameter to form at a rate of about 30 per second.

For Composition G, the flow rate was 0.4 kg/hour, giving non-jetting flow from the nozzle, and beadlets of about 4 mm diameter were formed at a rate of about 3 per second.

The oocyst-containing beadlets were stored in dessicators at 4° C. and 20° C. over poultry feed (about 65% RH). The viability of the oocysts was determined at weekly intervals by administering beadlets to poultry. In each instance, ten beadlets were given to each of a group of five 2-week old birds. In terms of the oocyst does, this represented a serious challenge and the oocyst output from the resulting infection was monitored. The results, expressed as the total oocyst output ($\times 10^6$) per bird over 5 days, are given in Table 3 below. These show that the oocyst viability remained at a high level for at least six weeks, and that significant number of the oocysts were still viable after 14 weeks.

TABLE 1

| COMPOSITION | % WATER | TOTAL OOCYST OUTPUT ($\times 10^6$) | R.I. ($\times 10^3$) | TOTAL OOCYST OUTPUT ($\times 10^6$) | R.I. ($\times 10^3$) | TOTAL OOCYST OUTPUT ($\times 10^6$) | R.I. ($\times 10^3$) |
| --- | --- | --- | --- | --- | --- | --- | --- |
| C | 0.5 | 3.76 | 19 | 17.6 | 54 | 0.056 | 0.23 |
| A | 8.5 | 7.31 | 59 | 8.7 | 42 | 0.5 | 3.2 |
| B | 16.5 | 5.94 | 32 | 17.0 | 56 | 1.9 | 9.5 |

TABLE 2

| | | | OOCYST OUTPUT ($\times 10^6$) PER BIRD | | | | | |
| --- | --- | --- | --- | --- | --- | --- | --- | --- |
| | | Storage | Storage time (weeks) | | | | | |
| Composition | Water (%) | Condition | 0 | 1 | 2 | 3 | 4 | 5 |
| D | 8 | Over water | 36.06 | 4.86 | 18.81 | 2.39 | 0.36 | −ve |
| E | 25 | " | 21.90 | 9.36 | 22.44 | 32.21 | 4.02 | 0.84 |
| D | 8 | Over feed | 36.06 | 12.24 | 25.20 | 25.10 | 2.94 | 1.84 |
| E | 25 | " | 21.90 | 25.29 | 9.12 | 8.24 | 2.52 | 1.41 |

TABLE 3

| | | OOCYST OUTPUT ($\times 10^6$) PER BIRD | | | | | | | |
| --- | --- | --- | --- | --- | --- | --- | --- | --- | --- |
| | Storage | Storage time (weeks) | | | | | | | |
| Composition | Temp | 0 | 1 | 2 | 3 | 4 | 5 | 6 | 14 |
| F (2 mm) | 4° C. | 2.5 | 2.6 | 4.6 | 2.9 | 2.0 | 0.7 | 4.1 | 1.8 |
| F (2 mm) | 20° C. | | 3.0 | 2.6 | 4.6 | 4.7 | 1.3 | 2.2 | 0.6 |
| G (4 mm) | 4° C. | | 2.3 | 3.0 | 6.3 | 6.0 | 2.3 | 4.3 | 5.7 |
| G (4 mm) | 20° C. | | 8.7 | 3.0 | 2.2 | 2.7 | | 8.3 | 0.2 |
| Contorl (1,000 fresh oocysts not in a bead) | | 2.7 | | | | | | | |

We claim:

1. A composition comprising dry free-flowing particles each consisting of a solid beadlet of lipid-continuous emulsion containing from about 25% to about 50% by weight water in a hardened palm kernel oil having a slip point in the range 35° to 45° C., each beadlet having an average diameter of about 2 to 3 millimeters and containing at least 1 viable sporulated oocyst of a species of coccidium infective to poultry, each beadlet having a protective coating of cement and/or gypsum, the protective coating having an average thickness of about 0.2 to 0.5 mm.

2. A composition comprising solid particles of a lipid-continuous emulsion of at least about 25% but not more than about 70% by weight water in lipid having a melting point in the range 30° to 55° C., the composition containing per particle an average of at least 1 live encysted parasitic protozoan.

3. A composition according to claim 2, wherein the lipid has a slip point in the range 35° to 45° C.

4. A composition according to claim 3, wherein the lipid or wax is a hardened palm kernel oil.

5. A composition according to claim 2, wherein the emulsion contains from 25 to 50% by weight water.

6. A composition according to claim 2, containing per particle an average of at least 1 viable sporulated coccidia oocyst.

7. A composition according to claim 2, wherein the particles are individually protected within a dry coating of at least about 0.1 mm thickness.

8. A composition according to claim 7, wherein the coating is formed from an inorganic powder which forms a hard composition when moistened and dried.

9. A composition according to claim 8, wherein the coating material is cement and/or gypsum.

10. A composition according claim 7, wherein the fat emulsion particles have a maximum dimension in the range of 2 to 5 mm, and the protective coating comprises a layer having a thickness in the range of about 0.2 mm to about 2 mm.

11. A composition according to claim 1, additionally incorporating a chemotherapeutic agent effective against the protozoa at an intermediate stage in their life cycle.

12. A feedstuff for poultry incorporating a particulate composition according to claim 1.

13. A process for preparing a composition according to claim 2, comprising the steps of preparing a dispersion of the encysted parasitic protozoa in a lipid-continuous emulsion, the emulsion being in the liquid state and at a temperature not exceeding 60° C., and causing the emulsion to set by cooling.

14. A process according to claim 13, wherein setting of the molten emulsion is achieved by contact with chilled water.

15. A process according to claim 14, wherein a stream of molten emulsion is released into a volume of cold water.

16. A process according to claim 13, wherein an initial aqueous emulsion of lipid is prepared and the parasitic protozoa are added to the preformed emulsion in a second mixing stage.

17. A process according to claim 13, wherein a coating is applied to the solid lipid-emulsion particles by tumbling the particles in an open vessel, spraying water or binder solution on to the tumbling particles whilst simultaneously adding a powdered coating material, and continuing this procedure until a sufficiently thick coat of the powdered material has formed on the particles.

18. A method of immunizing a domesticated animal against coccidiosis, in which method a composition according to claim 1, incorporating viable sporulated oocysts of a species of coccidium to which the animal is susceptible, is administered to the animal in an amount sufficient only to induce a sub-clinical infection.

19. A method of immunizing poultry, wherein a composition according to claim 1 is administered to the poultry in an amount sufficient only to induce a sub-clinical infection.

* * * * *